(12) United States Patent
De Polo (10) Patent No.: US 10,945,785 B2
(45) Date of Patent: Mar. 16, 2021

(54) DEVICE FOR TREATING THE LIGAMENTUM FLAVUM BY RADIO FREQUENCY

(71) Applicant: AMS GROUP SPA—SOCIETA' UNIPERSONALE, San Pietro Viminario (IT)

(72) Inventor: Giovanni De Polo, Spresiano (IT)

(73) Assignee: AMS GROUP SPA—SOCIETA' UNIPERSONALE, San Pietro Viminario (IT)

( * ) Notice: Subject to any disclaimer, the term of this patent is extended or adjusted under 35 U.S.C. 154(b) by 175 days.

(21) Appl. No.: 15/455,813

(22) Filed: Mar. 10, 2017

(65) Prior Publication Data

US 2017/0265935 A1 Sep. 21, 2017

(30) Foreign Application Priority Data

Mar. 16, 2016 (IT) ........................ 102016000027660

(51) Int. Cl.
*A61B 18/14* (2006.01)
*A61B 1/00* (2006.01)
(Continued)

(52) U.S. Cl.
CPC ...... *A61B 18/1477* (2013.01); *A61B 1/00165* (2013.01); *A61B 1/018* (2013.01); *A61B 18/1206* (2013.01); *A61B 18/1487* (2013.01); *A61B 18/148* (2013.01); *A61B 2018/0091* (2013.01); *A61B 2018/00196* (2013.01); *A61B 2018/00202* (2013.01);
(Continued)

(58) Field of Classification Search
CPC ............ A61B 18/1477; A61B 18/1206; A61B 2018/00339; A61B 2018/00202
See application file for complete search history.

(56) References Cited

U.S. PATENT DOCUMENTS 5,364,393 A * 11/1994 Auth ................... A61B 18/1492
606/34
2005/0101950 A1 * 5/2005 Gough ............... A61B 18/1477
606/41

(Continued)

FOREIGN PATENT DOCUMENTS

WO 2007080572 A1 7/2007

*Primary Examiner* — Michael F Peffley
*Assistant Examiner* — Bo Ouyang
(74) *Attorney, Agent, or Firm* — Volpe Koenig (57) ABSTRACT

A device for treating ligamentum flavum by radio frequency includes a hand grip and a cannula fixed at its proximal end to the hand grip extending longitudinally from the hand grip to an opposed distal end of the cannula configured to reach the ligamentum flavum. At least one electrode is electrically connectable to a radio frequency generator. The device also includes an actuating device of the electrode provided in the hand grip for moving the electrode. The actuating device includes a slider along a sliding guide having a first and a second sliding portion placed in succession. The first portion is shaped to allow an axial translation of the slider along the guide to generate a translation of the electrode in the cannula. The second portion is configured to allow rotational translation of the slider along the guide to generate a corresponding rotational translation of the electrode outside the cannula.

14 Claims, 6 Drawing Sheets

(51) Int. Cl.
  *A61B 1/018*   (2006.01)
  *A61B 18/12*   (2006.01)
  A61B 18/00    (2006.01)
  A61M 25/01    (2006.01)

(52) U.S. Cl.
  CPC ............... *A61B 2018/00339* (2013.01); *A61B 2018/00577* (2013.01); *A61B 2018/00946* (2013.01); *A61B 2018/00952* (2013.01); *A61B 2018/00982* (2013.01); *A61B 2018/1465* (2013.01); *A61B 2018/1475* (2013.01); *A61M 25/0136* (2013.01)

(56) References Cited

U.S. PATENT DOCUMENTS

| | | |
|---|---|---|
| 2010/0160911 A1 | 6/2010 | Ducharme |
| 2014/0121674 A1* | 5/2014 | Staunton .............. A61N 1/0558 606/129 |
| 2015/0148602 A1* | 5/2015 | Hill ................... A61M 25/0147 600/109 |
| 2016/0058489 A1 | 3/2016 | Fischell et al. |

* cited by examiner

DEVICE FOR TREATING THE LIGAMENTUM FLAVUM BY RADIO FREQUENCY

FIELD OF THE INVENTION

The present invention relates to a device for the ablation and decompression of the ligamentum flavum by radio frequency, having the characteristics as set forth in the preamble of the main claim.

The device of the invention is suitable to be used in the spinal endoscopy procedures in the epidural channel.

Furthermore, the device of the invention is particularly suitable to carry out the ablation and decompression of the ligamentum flavum.

BACKGROUND

The yellow ligaments, also known by the Latin name of ligamenta flava, compose, together with the interspinous, supraspinous, and intertransverse ligaments, the ligaments at a distance of the essential articulation of the vertebral column. These ligaments serve to join the vertebrae to one another, thus contributing to the stabilization and mobility of a bone to another bone.

The ligamentum flavum is present on the entire column, starting from the cervical portion up to the first sacral segment. For each vertebra, a pair of yellow ligaments is present, the thickness of which varies along the vertebral column.

In the neck region, the ligaments are thin, broad, and long. On the other hand, the ligaments are thicker the thoracic region, and this feature is further enhanced in the lumbar region.

The yellow ligaments are bundles of relatively elastic fibers extending between the lower margin of a vertebral lamina and the upper margin of the lower lamina. The marked elasticity of the yellow ligaments serves to preserve the upright posture, and to assist the vertebral column in its extension step following a flexion.

The yellow ligaments are the most elastic ligaments in the body; however, they tend to become stiffen and more fibrous due to a spinal degeneration process.

Such ligaments can become hypertrophic, i.e., they thicken and buckle into the underlying epidural channel, resulting in a narrowing thereof; such effect is referred to as a vertebral stenosis, and it involves a reduction in the dimensions of the channel where the nerve roots are housed, resulting in a compression thereof.

The compression of the nerve roots causes discomfort and increasing pain over time, and leads to a decrease in the mobility of the areas innervated by such roots.

The hypertrophy of the yellow ligaments mainly occurs at the lumbar portion of the vertebral column, where there is a high vertebral mobility, associated with high load forces.

Such a stenosis causes a compression of the lumbar nerve roots that from the spinal cord reach the lower limbs, and causes pain in the lumbar area and also in the lower limbs and specific regions thereof.

It is known to surgically intervene in the lumbar region of the vertebral column by inserting, for example, an interspinous spacer between the vertebrae affected by a stenosis so as to stretch the epidural channel, thus increasing the space within which the nerve roots run.

However, such surgical technique does not allow obtaining efficient, durable results, and it involves a main discomfort for the patient, since the spacer ultimately limits the mobility of the vertebral column by limiting the torsion/elongation/compression movements of vertebrae between which it is located.

Furthermore, the risk still remains that the spacer can be displaced or damaged, thus requiring a replacement.

Scalpels are known from, for example, CN2516107, for the incision of the ligamentum flavum. Such scalpels are inserted through an axial cutaneous cut at the vertebral area affected by stenosis, and moved so as to carry out a partial resection of the ligamentum flavum to clear the spinal channel.

A problem related to the use of such scalpels is that a very high working precision is required in order to avoid damaging the nerve roots and tissues underlying the ligamentum flavum; furthermore, such operation requires a long recovery and rehabilitation time for the patient.

A further problem related to the use of known scalpels is that such tools do not allow the operator to have a good visibility of the area to be treated; therefore, it is not possible to precisely control the cut depth of the scalpel.

Therefore, there is a risk to damage the patient's nerve roots, the integrity of which can be assessed only when the patients awakens.

In order to obviate such drawbacks, analgesic interventions have been proposed, the aim of which is to relieve and decrease the patient's pain, although without affecting the triggering causes of such pain.

Such interventions, which positively are less invasive and traumatic for the patient and also involve less risk, provide for the use of catheters that are suitable to dispense a drug in the area affected by the stenosis, or radio frequency (RF)-electrified needles of a continuous or pulsed type, acting on the area affected by the stenosis.

The radio frequency-electrified needles typically comprise a hand grip designed to be grasped by the surgeon, to which a peripheral venous catheter or a cannula is fixed, within which an electrode extends, which is connected to a radio frequency generator, and a sensor for detecting the temperature of the target tissue.

The insertion of the above-mentioned systems is monitored and controlled by radiological images.

The needle or the catheter are inserted percutaneously until reaching the spinal region affected by the stenosis, on which the analgesic treatment is to be carried out, i.e., to dispense the drug and/or carry out continuous or pulsed radio frequency therapies.

In the case of a continuous radio frequency, an electric field is applied only to the peripheral innervations (for example, those of the articular facets), which causes a temperature increase in the treated region of up to 80° C. Thus, an interruption of the pain signal is caused by burning the nerve fibers.

However, scientific studies showed that, over time, nerve fibers naturally self-repair and resume the pain signal transmission.

The Pulsed Radio Frequency (PRF) technique is also applicable to the central nervous system, since it is not detrimental to the nerve fibers. According to such a technique, an electric field is cyclically supplied at predetermined frequency (for example, for a period of 20 milliseconds for 2 cycles per second). In such a manner, a transient imbalance of the membrane potential is caused, which interrupts any pain signal transmissions.

However, the temperature of the affected tissues never exceeds 42° C., thus preventing a permanent damage of the nerve tissues or roots that are treated.

Since, as stated above, none of the above-mentioned analgesic treatments allows removing the trigger cause of the pain, the latter returns after some time.

Thus, the patient will undergo further treatment, with consequent discomfort and inconvenience.

Therefore, there is a clear need for a provision of an instrument that allows efficiently reaching and treating the ligamentum flavum in order to reduce possible stenoses or thickenings in a durable manner, while being safe for the patient.

Another object of the invention is to provide an instrument for treating the ligamentum flavum, which is easily controlled by the surgeon, while being efficient and not-invasive, hence, not potentially harmful either for the patient or the operator.

Another object of the invention is to implement a device, which allows an accurate treatment of the ligamentum flavum, and which allows precisely reaching the hypertrophic portions of the ligament causing the canal stenosis.

Still another object of the invention is to provide a device for treating the ligamentum flavum, which can be used with the systems currently known for spinal endoscopy.

SUMMARY

The problem underlying the present invention is to implement a device for treating the ligamentum flavum, which is structurally and functionally devised to allow overcoming the shortcomings set forth above.

This problem is solved by the present invention by means of a device obtained in accordance with the claims below.

BRIEF DESCRIPTION OF THE DRAWINGS

The characteristics and advantages of the invention will become more fully apparent from the detailed description of a preferred implementation example thereof, given by way of illustration but not limitation, with reference to the attached drawings, in which.

DETAILED DESCRIPTION OF THE PREFERRED EMBODIMENTS

In FIGS. 1-5, a device for treating the ligamentum flavum by radio frequency, obtained in accordance with the present invention is generally indicated with 1.

Figure 1:
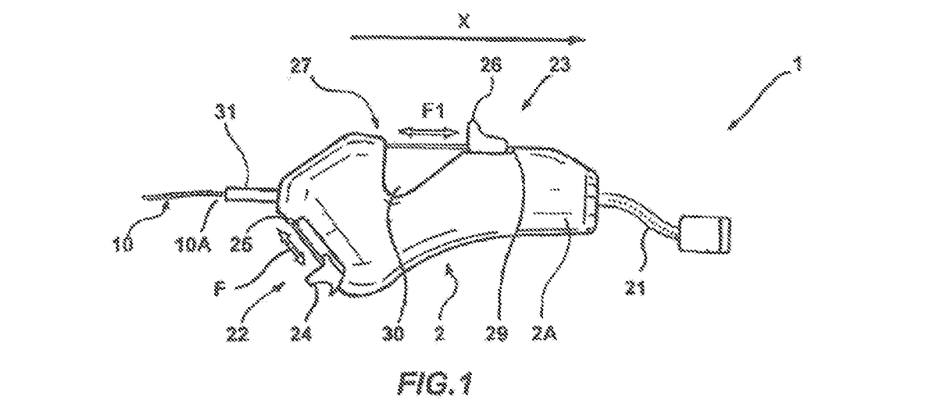
FIG. 1 is a schematic side view of a device for treating the ligamentum flavum obtained according to the present invention.

The device 1 is particularly suitable to act in the epidural space of a patient, i.e., in the area of the vertebral channel ranging from the ligamentum flavum to the dura mater. Such a channel has a reduced lumen and contains adipose tissue, veins, and small-sized arteries, lymphatic vessels, and thin bundles of collagen fibers, referred to as meningovertebral ligaments.

The device 1 comprises a hand grip 2 designed to be grasped by the surgeon to move the device 1, and a cannula 10 fixed at a first end 10A thereof, by a rigid joint 31, to the hand grip 2.

The rigid joint 31 is preferably made of metal.

The hand grip 2 has a body 2A designed to be grasped by the operator, preferably ergonomically shaped, so as to allow a convenient and firm grip of the device 1.

The hand grip 2 is provided with an attachment element 21, arranged to allow the attachment of the device 1 to an energy source with the aim of supplying the device 1. The attachment element 21 is positioned on the hand grip 2 preferably in an opposite position along the longitudinal axis X of the body 2A with respect to the rigid joint 31 and, thus, to the cannula 10.

Figure 2:
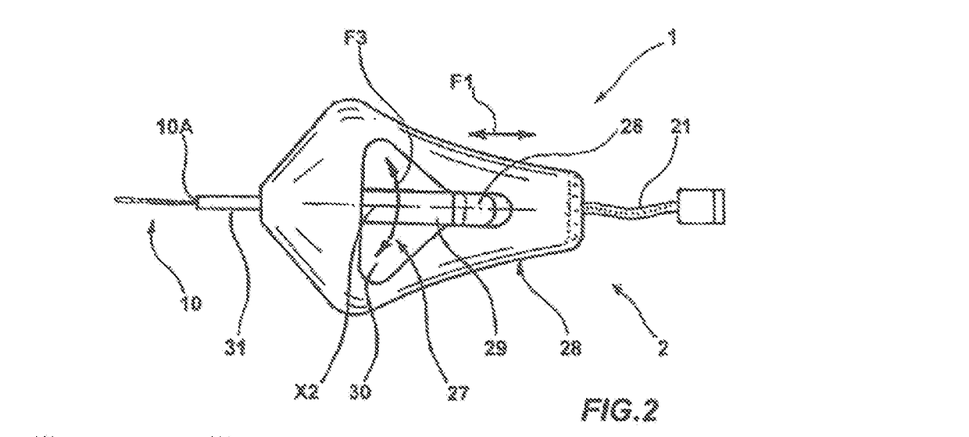
FIG. 2 is a schematic top view of the device of FIG. 1.
Figures 5, 6, 7:
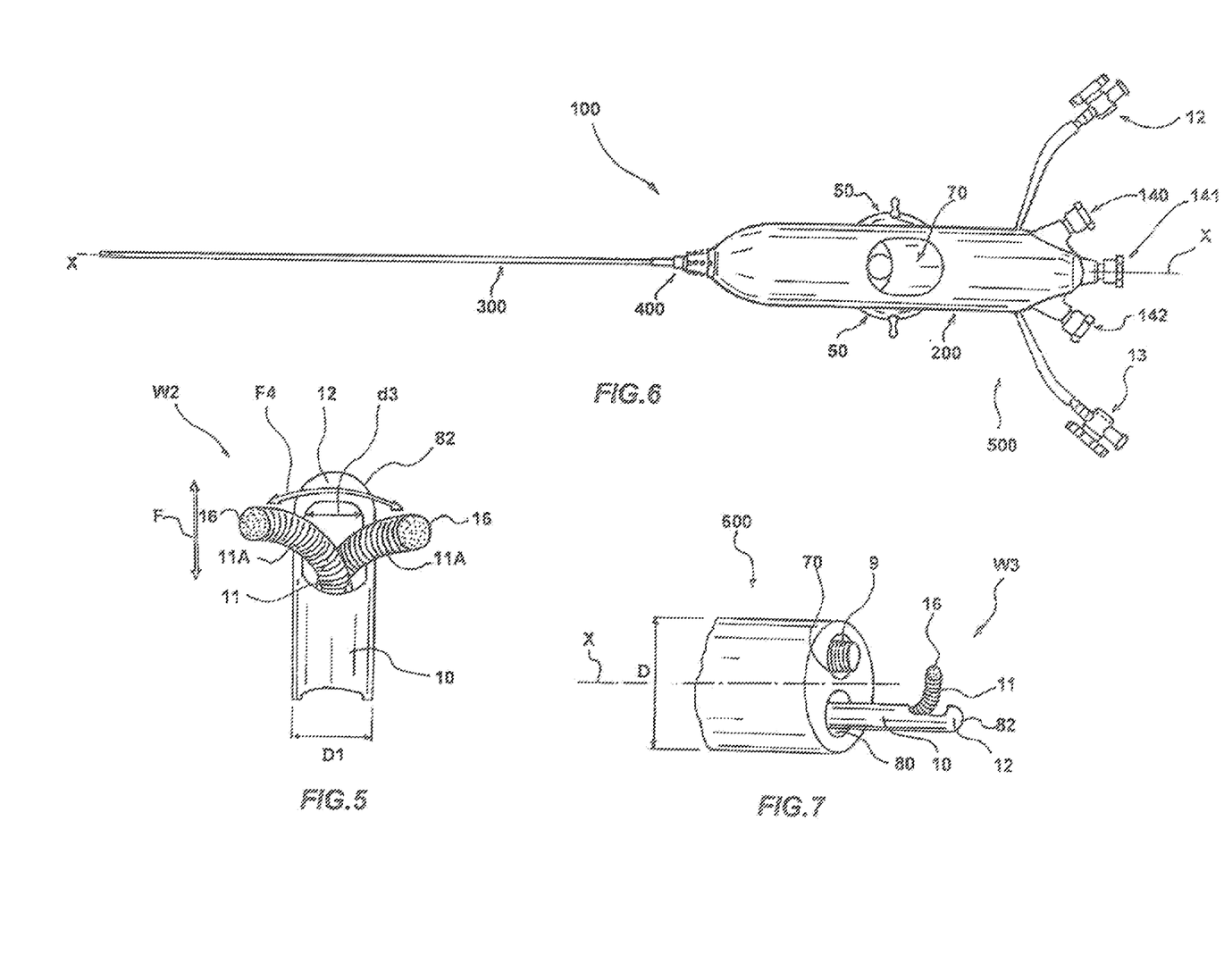
FIG. 5 is a top view of a detail of the device of the invention in a working operative configuration.
FIG. 6 is a schematic top view of an endoscopic spinal system.
FIG. 7 is a side view of a detail of the system of FIG. 6 in use with the device of the invention in an operative configuration.

The cannula 10, shown only schematically and in an interrupted manner in FIGS. 1 and 2, is shown in more detail in FIGS. 3 and 5.

Figures 3A, 4A:
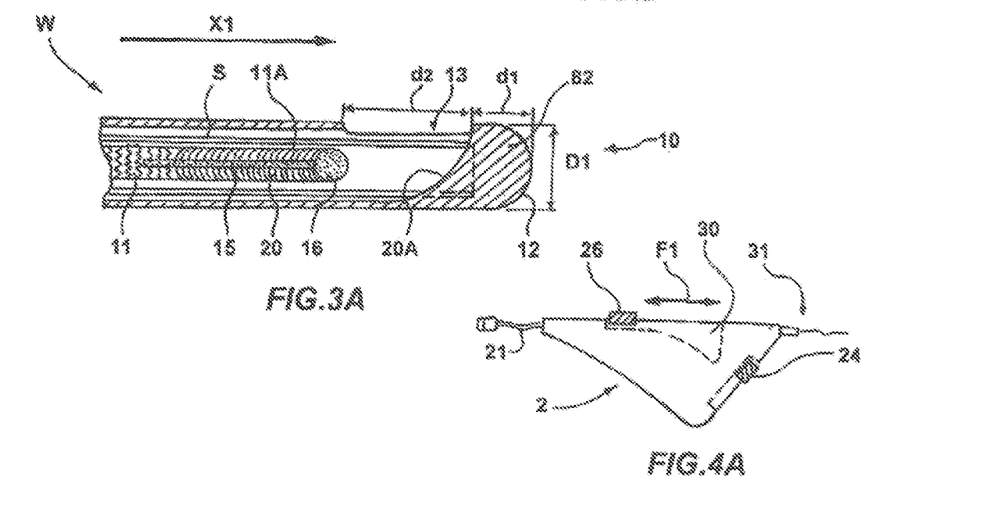
FIGS. 3A-3E are enlarged schematic views of a detail of the device of the invention in different operative configurations.
FIGS. 4A-4E are schematic side views of the device of FIG. 1 corresponding to the operative configurations of FIGS. 3A-3E respectively.

The cannula 10 has a preferably cylindrical shape, extending along a longitudinal axis X1 between the first end 10A connected to the hand grip 2 and an opposite second end 82.

The second end 82, which is designed to form the part of the cannula 10 located furthest from the hand grip 2, has an outer wall with a rounded profile.

The cannula 10 has an outer diameter D1 in the range from 0.4 to 1.5 millimeters.

Advantageously, the cannula 10 is made of polyamide or another suitable insulating material, for example, polypropylene, PVC, or Pebax.

The cannula 10 is internally provided with a longitudinal channel 20 extending along the longitudinal axis X1 of the cannula 10 itself, and designed to slidably house an electrode 11 and a sheath 18, as best explained herein below.

The cannula 10 further comprises a tip portion 12 arranged in the proximity of the second end 82 that is internally solid and made of a material ensuring an electric insulation, for example, polyamide (PA), TPE, preferably Pebax, or PVC.

The material of the tip portion 12, as well as the rounded profile of the second end 82, allow protecting the dura mater during the use of the device according to the invention, as best explained herein below.

The cannula 10 is movable so that the tip portion 12 can be moved away from/closer to the hand grip 2, as best explained herein below.

In particular, the second end 82 of the cannula 10 can be slid to be positioned at a distance from the hand grip 2 ranging from 0.5 mm to 50 mm.

Furthermore, on the outer wall S of the cannula 10, a side hole 13 is defined, which is positioned at a distance "d1" from the second end 82, ranging from 2 to 20 mm, and so shaped as to allow the passage therethrough of the electrode 11 and to allow it to partially emerge from the cannula 10, as best explained herein below.

Advantageously, the longitudinal channel 20 has a rounded end wall 20A so as to promote the sliding of the electrode 11 exiting towards the side hole 13.

Therefore, in the cannula 10, a tubular portion 10B extending between the first end 10A and the side hole 13; an intermediate portion 10C at the side hole 13; and a distal portion 10D ranging between the side hole 13 and the second end 82 can be identified.

Advantageously, the side hole 13 has a length "d2" as measured along the longitudinal axis X1 of the cannula 10, ranging from 0.5 to 4.0 millimeters, and preferably 2.5 millimeters, and a width "d3" as measured in the cross direction to the longitudinal axis X1 of the cannula 10, ranging from 0.4 to 1.5 millimeters.

The sheath 18 is cylindrical and extends between a proximal end, not shown, and a distal end 18B, and it is internally hollow so as to slidably house the electrode 11. The sheath 18 is slidable inside the longitudinal channel 20 in order to be movable with respect to the electrode 11 and the cannula 10. The sheath 18 is made of insulating material, preferably polyamide, polypropylene, PVC or Pebax.

The presence of the sheath 18 allows insulating and protecting the electrode 11 and avoiding accidental damages during the positioning and localization step of the area to be treated.

The electrode 11 is made of a metal material that is machined so as to confer a high elasticity, for example, AISI301 steel.

The electrode 11 is preferably of a monopolar type and it is electrically connectable to an outer radio frequency generator, per se known in the field, and not illustrated in the attached figures, by the attachment element 21 provided at the hand grip 2.

The electrode 11 is internally provided with an electrified wire 15 made of a deformable material designed to impart a desired angulation to the end portion 11A of the electrode 11, as best described below.

The electrified wire 15 is made of a material having a high elasticity, preferably a nickel/titanium-based alloy, in a particularly preferred version, Nitinol.

Such material has a good ductility, and biocompatibility; furthermore, it is superelastic or pseudoelastic, therefore it is particularly suitable to act as an actuator, recovering its original shape, or to exert even large forces onto the structures it is constrained to.

The electrified wire 15 can also be made of stainless steel.

The electrode 11 has preferably a diameter D4 in the range from 0.4 mm to 1.3 mm and it is provided at its end portion 11A with a treatment tip 16 having a spherical shape, preferably made of stainless steel, advantageously AISI 304.

Such a shape allows avoiding undesired damages to the part to be treated and the areas adjacent thereto, and/or the areas that the treatment tip can inadvertently contact, for example, during the positioning and localization step of the area to be treated.

As stated, the electrode 11 and the sheath 18 are slidable inside the longitudinal channel 20 along the longitudinal axis X of the cannula 10 independently of one another, i.e., they are mutually slidable, so as to be movable between several operative configurations of the treatment device 1, schematically shown in FIGS. 3A-3E.

The device 1 is movable between a rest configuration W, shown in FIG. 3A, in which the electrode 11 is entirely housed inside the longitudinal channel 20 and the sheath 18, and the treatment tip 16 is in a retracted position with respect to the side hole 13 and arranged inside the sheath 18. In such a configuration, the sheath 18 extends up to the tip portion 12 of the cannula to cover the side hole 13.

Such configuration is advantageously used in the positioning step and allows avoiding undesired damage to the patient's tissues.

Figure 3B:
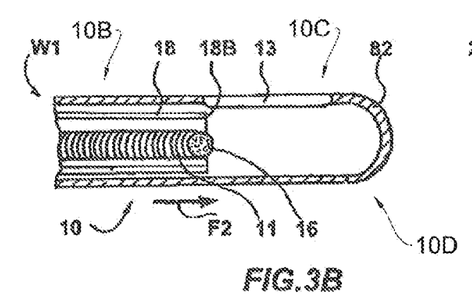

The device 1 is movable to a retracted configuration W1, shown in FIG. 3B, in which the electrode 11 is housed inside the longitudinal channel 20 and the sheath 18, but the latter is retracted so that its distal end 18B is positioned inside the longitudinal channel 20 in a retracted position with respect to the side hole 13, i.e., the side hole 13 is interposed between the distal end 18B of the sheath 18 and the second end 82 of the cannula 10. In such a manner, the access to the side hole 13 from the longitudinal channel 20 is clear, as best explained herein below.

Figure 3C:
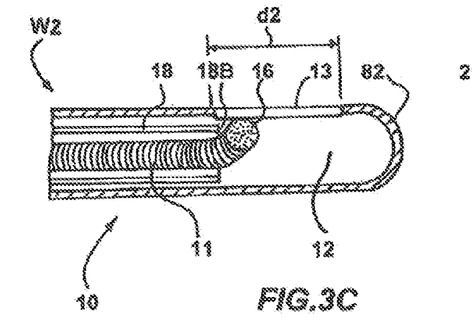

Furthermore, the device 1 is movable to an intermediate configuration W2, shown in FIG. 3C, in which the electrode 11 is partially extracted from the sheath 18 and the treatment tip 16 is arranged in the side hole 13 to the outside of the cannula 10.

Figure 3D:
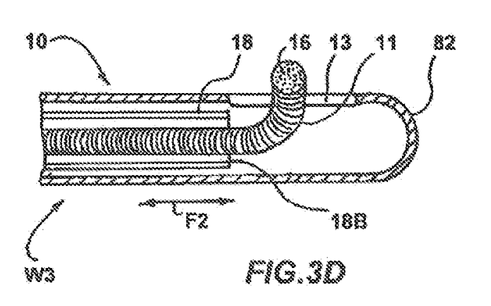
Figure 3E:
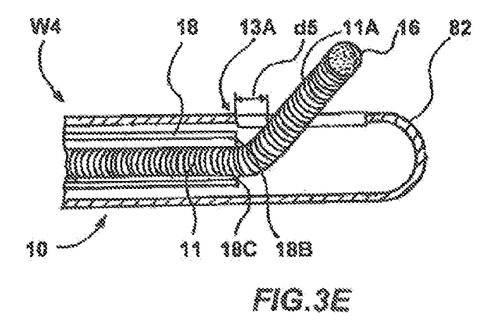
Figure 4B:
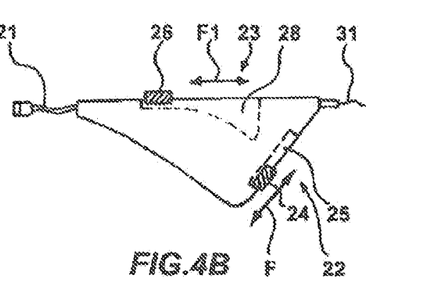
Figure 4C:
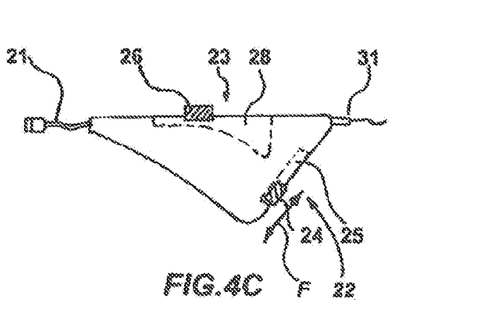
Figure 4D:
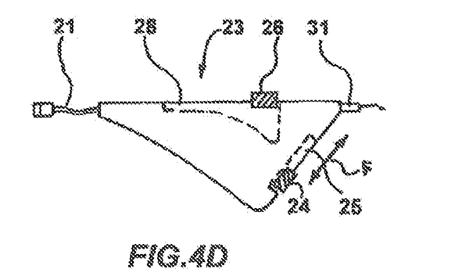
Figure 4E:
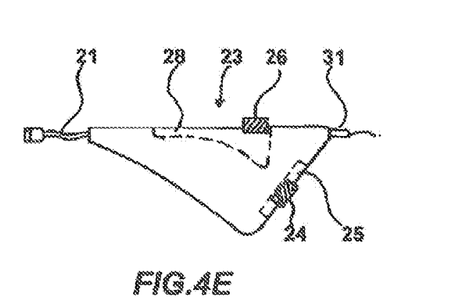

Furthermore, the device 1 is movable to several operative configurations, such as those shown in FIGS. 3D and 3E, respectively indicated with W3 and W4, in which the treatment tip 16 and the end portion 11A of the electrode 11 are arranged outside the cannula 10 and can be moved towards an area onto which the treatment is to be carried out.

In the second operative configuration W4, the sheath 18 is moved in the longitudinal channel 20 so as to be partially positioned at the side hole 13: its distal end 18C portion is located at the side hole 13. In such a manner, the sheath 18 takes a portion 13A of the extension side hole "d5" that cannot be used for the passage of the electrode 11. Therefore, the dimensions of the side hole 13 useful for the passage and the movement of the electrode 11 are reduced.

This allows limiting the mobility of the electrode 11, while increasing the accuracy during the treatment with the device of the invention.

Therefore, by moving the sheath 18 it is possible to vary the range of action of the electrode in the operative configuration and to vary the accuracy degree that can be achieved.

Advantageously, the electrode 11 in the operative configuration is extracted from the longitudinal channel 20 by a portion 11A having an extension up to 25 mm.

The actual extension of the extracted portion 11A of the electrode is adjusted based on the dimensions and characteristics of the portion to be treated.

Furthermore, on the body 2A of the hand grip 2, actuating devices to control and actuate the device 1 are provided, in particular, a first actuating device 22 to move the sheath 18, and a second actuating device 23 designed to move the electrode 11, and a third actuating device, not shown, to move the cannula 10.

The treatment device 1 further comprises transmission members not shown in the figures and designed to transmit the motion from the first and second actuating devices 22, 23, and the third actuating device, respectively, to the sheath 18, the electrode 11, and the cannula 10.

The first and second actuating devices 22, 23 are positioned on the body 2A of the hand grip 2 so that they can be advantageously actuated simultaneously, with different parts of a same hand by the operator.

The first and second actuating devices 22, 23 are positioned on the body 2A of the hand grip 2 so that an operator is able to actuate them alternately without releasing his/her hand from the hand grip, still continuing to maintain it with the same hand.

This allows increasing the device stability and the patient safety, in addition to the ease of use of the device of the invention by the operator, as best explained herein below.

The first actuating device 22 comprises a slidable button 24 and a groove 25 defined on the hand grip 2 and designed to compose the sliding seat of the slidable button 24. The groove 25 is dimensioned so as to allow the button 24 to slide in both directions of the arrow F of FIGS. 4B-4D.

By acting on the first actuating device 22, the sheath 18 is actuated by moving it along the longitudinal channel 20 inside the cannula 10 in both directions of the longitudinal axis X1, as indicated by the arrow F2, i.e., closer to, and away from, the tip portion 12 of the cannula 10, as best explained herein below.

The second actuating device 23 is arranged to move the electrode 11 so as to move it within the longitudinal channel 20 with respect to the cannula 10 and the sheath 18, as best described below.

The second actuating device 23 is shaped so as to be advantageously actuated with one of the fingers of the same hand with which the hand grip 2 is grasped.

The second actuating device 23 comprises a slider 26 slidable along a corresponding guide 27, which is so shaped as to allow and direct the sliding of the slider 26, as best described herein below.

The slider 26 is slidably coupled to the guide 27, so as to be able to slide in the guide 27 along a sliding axis X2, in both directions of the arrow F1 and to be able to rotate about such axis in both directions of the arrow F3 as best explained herein below.

The second actuating device 23 further comprises a cavity 28 defined on the body 2A at the guide 27 and designed to cooperate therewith to direct the sliding of the slider 26.

The cavity 28 comprises a first portion 29 and a second portion 30 positioned side-by-side along the longitudinal axis X of the body 2A and defining two adjacent and successive sliding portions for the slider 26.

In the version shown of the device of the invention, the sliding axis X2 is substantially parallel to the longitudinal axis X of the body 2A; however, in other versions of the device, such axes can be arranged transversely to each other.

The first portion 29 of the cavity 28 is shaped so as to couple by a shape coupling to the guide 27, to allow the sliding of the slider 26 only along the sliding axis X2 of the guide 27 and to substantially prevent other displacements thereof.

The second cavity portion 30 has a larger extension with respect to the guide 27 in the direction transversal to the sliding axis X2, in such a manner that, at the second cavity portion 30, both the sliding of the slider 26 along the sliding axis X2 and a rotation of the slider 26 on the guide 27 about such sliding axis X2 are allowed.

In other terms, the slider 26 can perform a rotational translation along the second cavity portion 30.

The second cavity portion 30 advantageously has such an extension as to allow a rotation of the slider 26 about the sliding axis X2 of the guide 27 through an angle in the range from about 90° to about 180°.

When the slider 26 is moved along the portion of the guide 27 located at the first portion 29 of the cavity 28, the electrode 11 is advanced along the longitudinal channel 20 and progressively moved from the rest configuration W or the retracted configuration W1, in which the electrode 11, and particularly the treatment tip 16, are housed inside the longitudinal channel 20 in a retracted position with respect to the side hole 13, to an intermediate configuration W2, in which the electrode 11 is still housed inside the longitudinal channel 20 and the treatment tip 16 is positioned at the side hole 13.

By continuing to move the slider 26 along the guide 27, particularly along the portion of the guide 27 located at the second portion 30, the electrode 11 is progressively pushed through the side hole 13 and made to progressively emerge from the cannula 10 to an operative configuration W3.

In such configuration, the treatment tip 16 and a portion of the electrode 11A that is contiguous to the treatment tip 16 are positioned outside the cannula 10. Therefore, the treatment tip 16 can be oriented and directed, by acting on the slider 26, to bring it towards the and in contact with the area to be treated.

At the second portion 30, it is possible to move the slider 26 along the guide 27 in both directions of the sliding axis X2 in order to move the electrode 11 along the longitudinal axis X1 of the cannula 10 in both directions of the arrow F2, as indicated in FIG. 3D, to suitably position the treatment tip 16. Furthermore, in the second portion 30 it is possible to rotate the slider 26 about the guide 27, in order to rotate the electrode 11 and, in particular, the treatment tip 16 with respect to the longitudinal axis X1 of the cannula 10, as shown by the rotation arrow F4 in FIG. 5.

In such a manner, the treatment tip 16 can be efficiently moved and directed towards the area to be treated.

The above-mentioned displacements are carried out without a need to have to move the cannula 10, but only the electrode 11 inserted inside the latter.

Therefore, the patient's discomfort is reduced, and the safety of use of the device of the invention is increased, which maintaining the dura mater in a safe downward position.

The second actuating device allows efficiently positioning the treatment tip 16 in a markedly broad treatment area.

By varying the extension of the portion of electrode 11A that is positioned outside the cannula 10, the dimensions of the treatment area that can be efficiently reached with the treatment tip 16 vary.

By varying the dimensions and shape of the side hole 13, the dimensions of the treatment area that can be efficiently reached by the treatment tip 16 can be varied.

With the device 1 of the invention a precise positioning of the treatment tip 16 is achieved; again, it is further possible to reach, without moving the cannula 10, a markedly broad treatment area of the ligamentum flavum.

Furthermore, by moving, by means of the first actuating device 22, the sheath 18 with respect to the electrode, it is possible to vary the extension d5 of the portion 13A of the side hole 13 that is taken by the sheath 18 and, vice versa, the dimension of the side hole 13 portion that is free for the passage and the movement of the electrode 11, thus increasing the movement/angulation precision of the treatment tip 16 exiting the side hole 13.

By reducing the dimension of the free portion of the side hole 13, the actuation precision of the electrode 11 is incremented, and the dimensions of the area that can be reached and treated by the electrode 11 are reduced.

Furthermore, the rounded shape of the treatment tip 16 allows avoiding damaging areas which the tip would accidentally contact during the positioning thereof.

On the contrary, in the first portion 29 of the cavity 28, the slider 26 can be moved along the guide 27 only in both directions of the sliding axis X2 to move the electrode 11 along the longitudinal axis X1 of the cannula 10 in both directions of the arrow F2.

In such a manner, undesired distortions or windings of the electrode 11 which would adversely affect the subsequent orientation thereof are avoided.

Therefore, the configuration of the cavity 28 allows improving the actuation of the electrode 11, increasing the precision and safety of use of the device 1.

Such configuration of the cavity 28 allows at the same time to obtain, for the treatment device of the invention, a very high range of action for the electrode, while maintaining a reduced invasiveness.

The treatment device 1 of the invention is suitable to be used with an endoscopic treatment apparatus, such as the one shown in FIG. 6, designed to act in the epidural space, i.e., in the area of the vertebral channel ranging from the ligamentum flavum to the dura mater, as best explained herein below.

Figure 9:
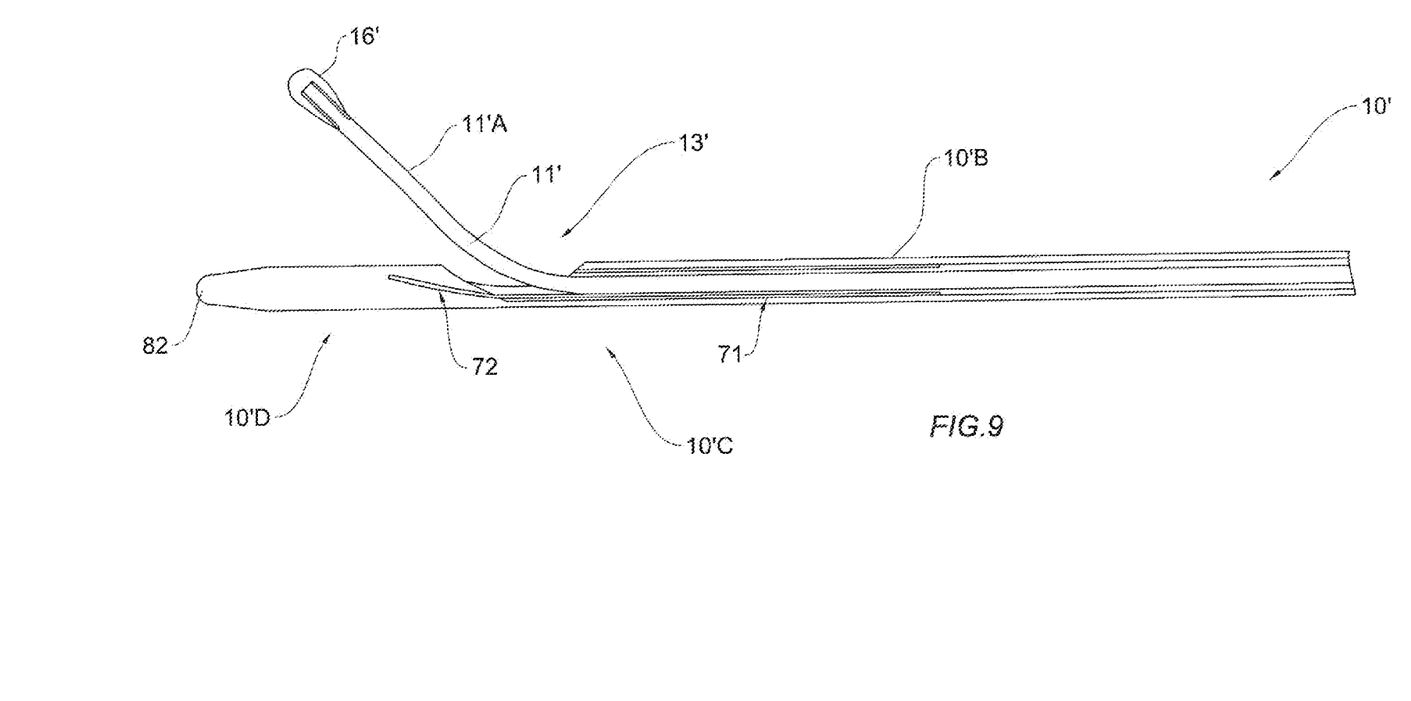
FIG. 9 is a schematic view of a detail of the device of the invention provided with the insert of FIG. 8 in a determined operative configuration.

In FIG. 9, an alternative version of a cannula 10' to be used with the device of the invention is schematically shown.

Parts corresponding to the above-described cannula will be designed with corresponding numeral references, followed by a superscript, and they will not described in detail.

In such a version, the cannula 10' houses, in its longitudinal channel 20', the electrode 11' slidably inside the longitudinal channel 20', and also a reinforcing sheath 700.

Figure 8:
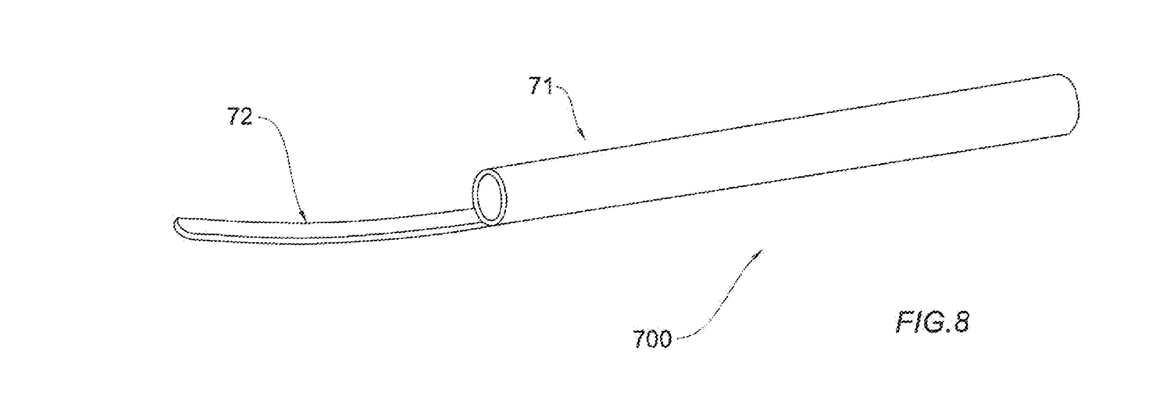
FIG. 8 is a schematic view of an insert to be used in the device of the invention.

The reinforcing sheath 700, shown in more detail in FIG. 8, is made of stainless steel or another suitable reinforcing material, such as, for example, polycarbonate or PEEK.

The reinforcing sheath 700 comprises a tubular body 71 having a length ranging from 2-7 cm, preferably between 3-4 cm, in which the electrode 11' is slidably housed, and a reinforcing appendix 72 extending from the tubular body 71 and designed to reinforce the electrode 11' and to guide the movement thereof.

The reinforcing sheath 700 is positioned in the longitudinal channel 20' of the cannula 10' in such a manner that the tubular body 71 is housed in the tubular portion 10'B of the cannula 10' and the reinforcing appendix 71 is housed at the intermediate portion 10'C and the distal portion 10'D.

The reinforcing sheath 700 is positioned in the longitudinal channel 20' in such a manner that the reinforcing appendix 72 is positioned in a position transversely opposite the side hole 13', i.e., so that the reinforcing appendix 72 faces the side hole 13' and does not obstruct it.

The reinforcing appendix 72 is curved, with its concavity facing the electrode 11' so that, when moving away from the tubular portion, it gets closer to the electrode.

Alternatively, the reinforcing appendix 72 is inclined so that, when moving away from the tubular portion, it gets closer to the electrode.

The reinforcing appendix 72 allows directing the movement of the electrode 11', in particular when it emerges through the side hole 13.

The presence of the reinforcing sheath 700 allows minimizing the tensions applied to the electrode and reducing the torsional stress applied onto the electrode 11'.

The presence of the reinforcing sheath 700 allows reinforcing the end part of the cannula 10', without excessively stiffen the entire the body of the sheath 10'.

In other words that part of the cannula 10', which is subjected to larger tension or torsion stresses is reinforced.

The presence and shape of the reinforcing appendix 72 allow directing the displacement of the electrode 11' emerging from the side hole 13 and also during the actuation to carry out an ablation procedure.

Furthermore, the presence and the configuration of the reinforcing appendix 72 in the distal portion 10'D of the cannula 10' allows reinforcing such part, while avoiding to generate traumas to the patient, since the latter only contacts the cannula 10'.

In some versions, the reinforcing sheath 700 can be slidable inside the longitudinal channel and can be actuated through corresponding actuating devices provided on the hand grip of the device.

In such a version, the reinforcing sheath 700 can be translated along the longitudinal axis X1 of the cannula 10' and/or rotated inside the longitudinal channel 20' with respect to the longitudinal axis X1 to vary the shape and opening of the side hole 13' available for the passage of the electrode 11'.

In another version, not shown in the figures, the electrode, the reinforcing sheath, and the slidable sheath are housed inside the longitudinal channel, the reinforcing sheath being interposed between the electrode and the sheath.

Figure 10:
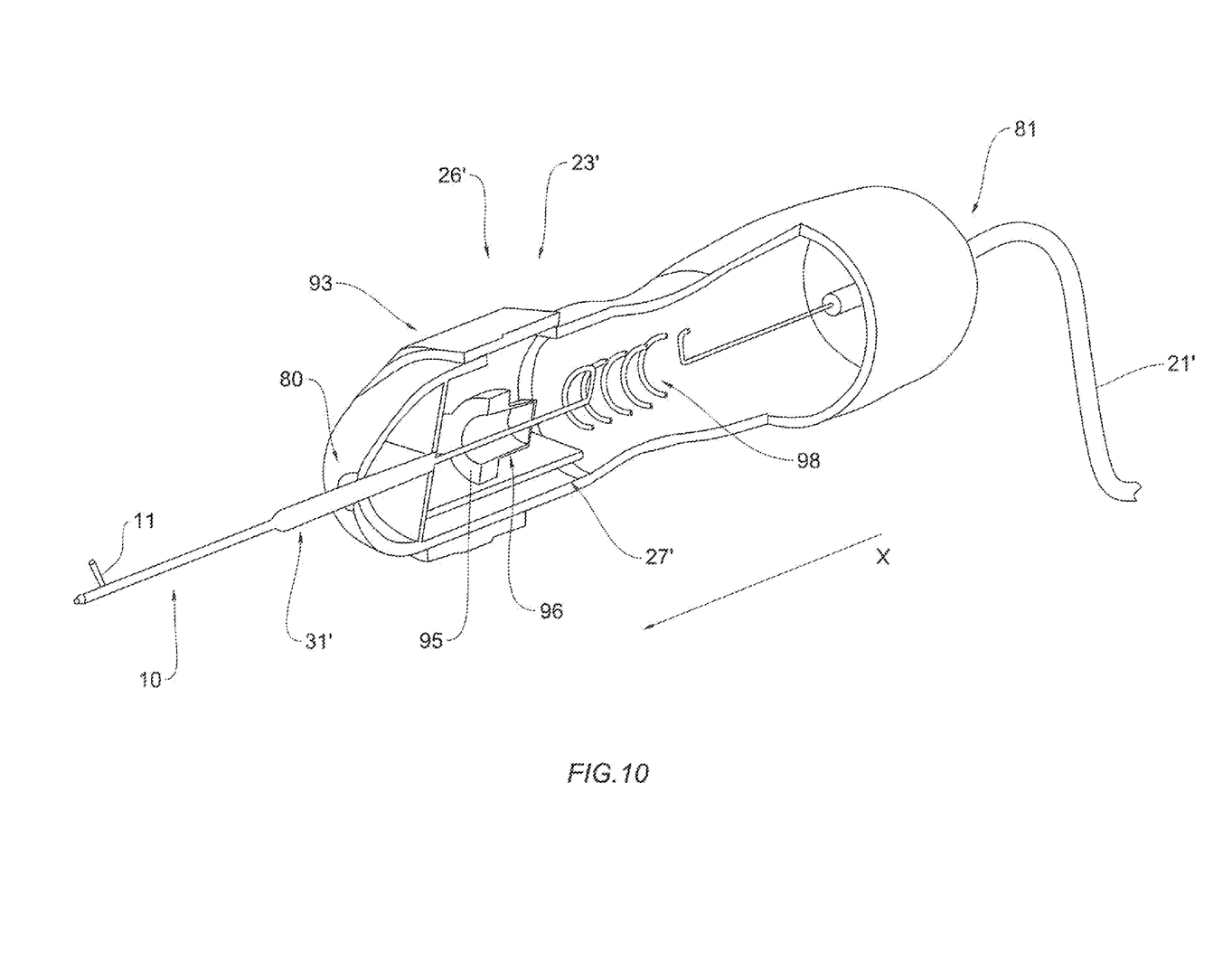
FIG. 10 is a schematic view of an alternative version of the device according to the invention.
Figures 11, 12:
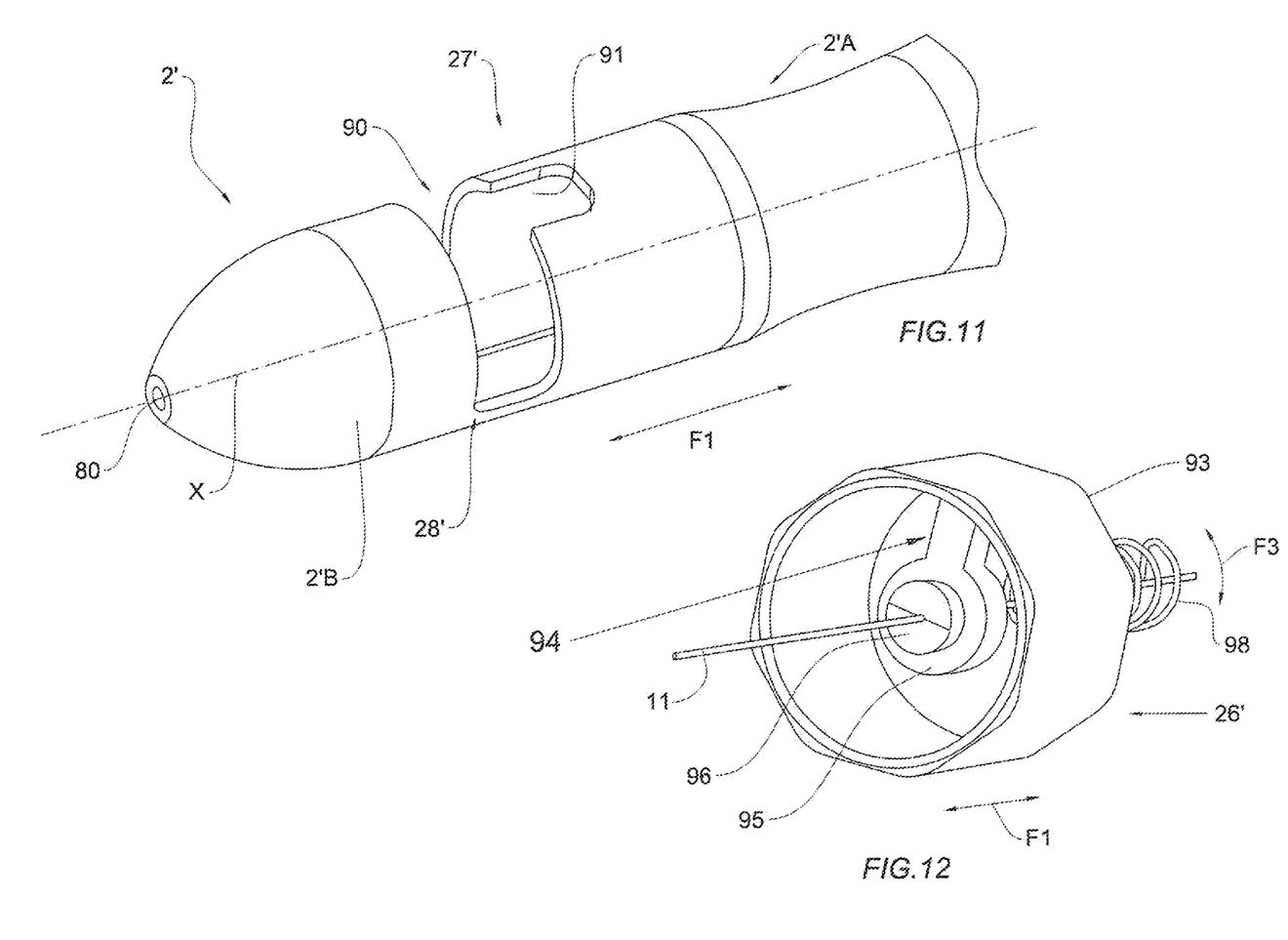
FIGS. 11 and 12 are schematic views of two distinct details of the device of FIG. 10.

In FIGS. 10-12, an alternative version of the treatment device 1' of the invention is shown, in which parts corresponding to the above-described version of the device will be not described in detail, and they will be indicated with corresponding numeral references followed by a superscript.

The treatment device 1' of FIGS. 10-12 is distinguished from the one shown in the preceding figures by the shape of the body and the configuration of the actuating devices 23' to move the electrode 11, as best explained herein below.

In the attached figures of such version of the treatment device, neither the devices for the actuation of the slidable sheath, nor the actuating device for moving the cannula are shown; however, such actuating devices can be provided also with such embodiment of the treatment device.

Such version of the device can be used, as well as the version of the device of FIGS. 1-7, both with the cannula shown in FIGS. 3A-3E and with the cannula shown in FIGS. 8 and 9, with or without a sheath and/or with or without a reinforcing sheath.

On the other hand, also in such version, transmission members are provided to transmit the motion from the actuating devices respectively to the sheath, where provided, the electrode, and the cannula.

The hand grip 2' of the treatment device 1' of FIGS. 10-12 is designed to be grasped by the operator for moving the device 1' and has an elongated shape, preferably with a circular section.

Such a shape allows promoting the grip and handling of the device 1' by the operator.

Advantageously, the body 2'A has a variable circular section along the longitudinal axis X thereof to promote a firm grip by the user.

The body 2'A is provided at the two opposite longitudinal ends thereof with two distinct openings 80, 81, respectively for the grafting of the rigid joint 31' which the cannula 10 is fixed to, and the attachment element 21' for the connection to an energy source, such as a radio frequency generator.

The body 2'A is internally hollow for housing the electrified wire 15' and the electrode, which preferably extend in the direction of the longitudinal axis X inside the body 2'A.

An electrical connection cable 98 extending between the electrified wire 15' and the attachment element 21' is also housed inside the body 2'A, which cable is arranged to electrically connect the electrified wire 15' and the attachment element 21'.

Advantageously, the electrical connection cable 98 is at least partially coil-wound to compensate the movements of the electrified wire 15' and to allow the passage of current at any position thereof.

Such expedient can be also provided in the version of the device of FIGS. 1-7.

The treatment device 1' is also provided with a actuating device 23' associated with the body 2'A so as to be displaceable with respect to the body 2'A to move the electrode 11', as best explained herein below.

In such version, the actuating device 23' comprises an actuating ring nut 26' provided with a grip portion 93 adapted to be fitted on the body 2'A so as to be able to slide with respect to the body 2'A, a control ring 95 positioned inside the body 2'A, and an actuating slider 94 extending from the grip portion 93 inside the body 2'A so as to be interposed between the grip portion 93 and the control ring 95.

In the version shown, the sliding axis X2 of the actuating ring nut 26' is substantially parallel to and coincident with the longitudinal axis X of the body 2'A; however, in other versions of the device such axes can be arranged transversely to one another or arranged parallel to one another and spaced apart one from the other.

The grip portion 93 is ring-shaped so as to affect the entire circumference of the body 2'A.

Such configuration considerably simplifies the actuation of the device by the operator, since it is possible to actuate the actuating device, thus moving the electrode, independently of the orientation of the device in the operator's hand.

Furthermore, such version of the device is suitable to be used with the right or left hand equally.

A guiding groove 27' is provided on the outer surface 2'B of the body 2'A, suitable to allow and direct the movement of the actuating ring nut 26'.

The guiding groove 27', best seen in FIG. 11, comprises a transversal groove 90 extending by an arc of circumference defined by an angle at the center in the range from 90°-270°, and a longitudinal groove 91 with length "L1" ranging from 0.5 cm to 5 cm defined in the longitudinal direction of the body 2'A.

The longitudinal groove 91 opens towards the transversal groove 90, so as to compose two adjacent and consecutive lengths along the longitudinal axis X of the body 2A and to generate a single sliding cavity 28', which forms the seat and the sliding guide for the actuation of the electrode 11', as best explained herein below.

The actuating slider 94 is dimensioned so as to couple by a shape coupling with the longitudinal groove 91, as best explained herein below.

In particular, the actuating slider 94 and the longitudinal groove 91 are dimensioned so that the actuating slider 94 is received in the longitudinal groove 91 with the ability of translate along the longitudinal axis X in both directions of the arrow F1, but a rotation thereof about such axis is substantially prevented.

Advantageously, the actuating slider 94 has a length "L2" along the longitudinal axis smaller than the longitudinal dimension of the transversal groove 90, so that some translation of the actuating slider 94 along the longitudinal axis X is allowed to the transversal groove 90.

The actuating slider 94 is further dimensioned so as to be able to rotate about the longitudinal axis by sliding inside the transversal groove 90, in both directions of the arrow F3. As stated above, the transversal groove 90 is first dimensioned so as to allow a rotation of the actuating slider 94 ranging from 90° to 270°.

The control ring 95 is coupled to the electrode 11 so that a movement of the control ring 95 generates a corresponding movement of the electrode 11.

Advantageously, a gasket 96 is interposed between the control ring 95 and the electrode, to make the coupling between the control ring 95 and the electrode 11 firmer, in order to make them integral when they are moved.

This allows increasing the device stability and the patient safety, in addition to the ease of use of the device of the invention by the operator, as best explained herein below.

The actuating ring nut 26' is slidably coupled to the sliding cavity 28' so that the longitudinal groove and the transversal groove define two adjacent and successive sliding portions for the actuating ring nut 26'.

The actuating slider 94 is shaped so as to couple by a shape coupling to the longitudinal groove 91, to allow the sliding of the actuating ring nut 26' only along the longitudinal axis X and to substantially prevent other movements thereof.

On the contrary, when the actuating slider 94 is brought at the transversal groove 90, both the sliding of the actuating ring nut 26' along the sliding axis X2 and a rotation of the slider actuating ring nut 26' about such sliding axis X2 are allowed.

In other terms, at the transversal groove 90, the actuating ring nut 26' can perform a rotational translation.

The apparatus 100 shown in FIG. 6 comprises a handle 200 designed to be grasped by an operator, a catheter 300 fixed at its first proximal end 400 to the handle 200, and control members operatively connected to the catheter 300 and designed to move and block the catheter 300, as best explained below.

The catheter 300, shown in more detail in FIG. 7, has a preferably cylindrical shape and extends along a longitudinal axis X' between the proximal end 400 and a distal end 600 axially opposed to the proximal end 400.

The catheter 300 has a length L ranging from 20 to 60 centimeters, and preferably 30 centimeters, and a circular section with a diameter "D" in the range from 2.0 to 4.0 millimeters, and preferably about 3.3 millimeters.

The catheter 300 is advantageously made of a flexible material, such as, for example, Pebax, or polyamide.

The catheter 300 is internally hollow and provided with a pair of longitudinal channels 70, 80 coaxial with the longitudinal axis X' of the catheter 300, positioned preferably in a diametrically opposite position, as can be seen in FIG. 7, extending along the entire length of the catheter 300.

One of the two longitudinal channels is designed to house, allowing the sliding thereof, a viewing element 9 which is fixed to the proximal end 400 of the catheter 300 and which is slidable in the longitudinal hole 70 so as to extend up to the distal end 600 to allow the visualization of the area around the distal end 600.

The viewing element is, in the preferred form, a flexible optical fiber extending inside the longitudinal hole 70 of the catheter 300 along the longitudinal axis X' thereof.

The use of an optical fiber allows not to alter the flexibility of the distal end 600 of the catheter 300, while obtaining an angle of view of about 90°, and to carry out the lighting of the area around the distal end 600.

The images taken by the viewing element 9 are advantageously provided to the operator on a displaying device that is operatively connected to the viewing element 9 and arranged outside the apparatus 100, for example, a screen or a monitor, not shown.

The second longitudinal channel 80 is arranged to slidably house treatment instruments to be used in the treatment apparatus 100, for example, micro-balloons for the expansion of the channel, "micrograspers" for a biopsy of the adhesive tissue, probes for coagulation of cicatricial tissue, etc.

The second longitudinal channel 80 is shaped so as to slidably house the cannula 10, or 10' of the treatment device 1 of the invention, as best described herein below and as shown in FIG. 7.

The moving members of the treatment apparatus 100 comprise, in the version shown, moving levers 50 actuatable to orient the distal end 600 of the catheter 300 during the movement thereof, and a locking mechanism 702 designed to be actuated to lock the distal end 600 at a desired position, thus ensuring the operator an improved dexterity during the surgical procedure, since he/she can release his/her hands from the hand grip 200 of the device 100 in order to engage in the movement of the instruments that are housed in the hole 80.

Furthermore, the handle 200 is provided with a plurality of connecting elements 500 designed to connect the treatment apparatus 100 to various endoscopic treatment devices to carry out the desired endoscopic treatments.

The handle 200 is internally provided with connecting channels, not shown in the figure, and designed to connect each connecting element to the second longitudinal channel 80 to allow the insertion of the endoscopic treatment device therein and/or to allow providing the desired treatment at the distal end 600.

Such treatment devices may comprise, for example, devices supplying a fluid, such as a physiological solution, drug supply devices, or devices for collecting excess fluid, as best described herein below.

The connecting elements 500 are provided on the handle 200 preferably in a position axially opposite to, or in any case suitably spaced from the catheter 300 and the moving members so as not to hamper the exact hand grip of the handle 200 and the actuation of the treatment apparatus 1 by the operator.

The connecting elements 500 are provided with hemostasis valves to be able to sealingly clamp the channels, so as to be able to secure the various tools and prevent a liquid backflow.

The connecting elements 500 comprise, in the shown version of the treatment apparatus 100, three introducers 140, 141, 142 provided on the handle 200 preferably in a position axially opposite to the catheter 300, designed to allow the connection to the treatment apparatus 1 of treatment devices, such as, for example, the device 1 for treating the ligamentum flavum of the invention, to carry out endoscopic treatments.

Each introducer 140, 141, 142 is operatively connected to the second longitudinal channel 80; two introducers are usually designed to allow the insertion of the desired endoscopic treatment device into the longitudinal channel 80, while the third introducer, typically the central introducer 141, is intended for the insertion of a visualization instrument.

Furthermore, the handle 200 is provided with a fluid supply valve 12, operatively connected to the first longitudinal channel 70, and arranged to connect the handle 200 to a fluid reservoir, such as physiological solution, or a drug, inter alia, to be directed into the first longitudinal channel 70 towards the area to be treated.

Furthermore, the handle 200 is provided with a discharge valve 13 to allow discharging excess liquids coming from the epidural channel itself, which flow back from the area to be treated through the second longitudinal channel 80 and the handle 200. The discharge valve 13 can be connected to a bag for the collection of excess liquids coming from the epidural channel itself.

In such a manner, the generation of overpressures inside the epidural channel is prevented.

In order to carry out treatments via the endoscopic spinal route, an operator first provides for drilling an access hole to the spinal channel at the sacral hiatus by means of a peripheral venous catheter and inserting a guide wire into the peripheral venous catheter to maintain the correct access trajectory.

Next, while leaving the guide wire in situ, the operator proceeds to the expansion of the sacral region and to position an operative sleeve into the access hole.

Next, the operator grasps the handle 200 of the treatment apparatus 100, introduces the catheter 300 into the hole previously drilled, and begins to move it along the spinal channel by acting on the moving levers 50, so as to progressively displace the distal area 600 of the catheter 300 along the spinal channel to bring it to the proximity of the area to be treated.

The images provided by the viewing element 9, which is inserted and locked in the catheter 300 through the introducers 141, allow directing the operator in moving the catheter 300 along the spinal channel. In fact, during the movement of the catheter 300 in the spinal channel, the operator controls the position reached thereby through the images provided by the viewing element 9 on the outer displaying device and possibly by radiological images.

The catheter 300 is inserted and moved until it reaches the area to be treated, particularly, the spinal level exhibiting the ligamentum flavum hypertrophy to be treated.

When the distal portion 600 of the catheter 300 has reached the area to be treated, the operator locks the catheter 300, hence the distal portion 600 thereof, acting on the locking mechanism 702. Subsequently, the operator connects a treatment device, for example the treatment device of the invention, to the treatment apparatus 100, via one of the introducers 140, 142.

To do this, the operator inserts the cannula 10, or 10' into the hole of one of the introducers and advances the tip portion 12 into the second longitudinal hole 80 up to the distal portion of the catheter 600.

The cannula 10, or 10', is advanced into the second longitudinal hole 80 until when the tip portion 12 can be seen by the optical fiber 9 and, therefore, in the images provided on the outer visualization device.

Advantageously the second end 82 of the cannula 10, or 10', can be advanced by sliding, until being positioned at a distance of 50 mm from the distal portion 600 of the hand grip 200.

When the tip portion 12 has been advanced up to the distal end 600 of the catheter 300 so that the side hole 13 is arranged outside the second longitudinal hole 80 and can be seen by the optical fiber 9, the operator provides to clamp the introducer 140 or 142 which the treatment device 1, or 1' has been connected to, in order to lock the treatment device 1, or 1' itself and the cannula 10 in the desired position.

Subsequently, the operator actuates the slider 24 to move the sheath 18 from the rest position W towards the retracted position W1, i.e., so as to release the side hole 13 from the sheath 18. Subsequently, the operator acts on the slider 26 by moving it along the guide 27 to progressively slide the electrode 11 into the cannula 10 to move the treatment tip 16 to the side hole 13 and subsequently outside thereof, in order to make it progressively emerge from the cannula 10.

The slider 26 is first moved along the first portion 29 of the cavity 28 to bring the electrode 11 from the retracted configuration W1 up to the intermediate configuration W2, by bringing, i.e., as described above, the treatment tip 16 to the side hole 13.

As stated above, along such movement, the slider 26 and, consequently, the electrode 11, can move only axially.

Subsequently, the operator continues to move the slider 26 along the second portion 30 of the cavity, thus making progressively the electrode 11 and in particular the treatment tip 16 emerge through the side hole 13.

Along the second portion 30, as stated above, the operator can move the slider along the guide 27, and also rotate it about the longitudinal axis X2 of the guide 27 itself, hence also rotating the treatment tip 16.

Similarly, in the case that the treatment device 1' of FIGS. 10-12 is used, one provides to move the actuating ring nut 26' in the direction of the longitudinal axis X, moving the actuating slider 94 first along the longitudinal groove 91, to bring the electrode 11' from the retracted configuration W1 to the intermediate configuration W2, by bringing, i.e., as described above, the treatment tip 16 to the side hole 13.

As stated above, during such movement, the actuating ring nut 26' and, accordingly, the electrode 11', can move only axially.

Subsequently, the operator continues to move the actuating ring nut 26' along the transversal groove 90, thus making progressively the electrode 11' and in particular the treatment tip 16 emerge through the side hole 13.

Along the transversal groove 90, as stated above, the operator can move the actuating ring nut 26' both translationally along the longitudinal axis X, and also rotating it about the longitudinal axis X of the treatment device 1' itself, hence by rotating also the treatment tip 16.

Consequently, in both cases, the electrode 11 can be pushed outside the side hole 13, with various moving trajectories, and the treatment tip 16, can be moved towards a possible area to be treated with relatively large dimensions. Therefore, without moving the cannula, the treatment of a broad region of the ligamentum flavum can be efficiently carried out.

Furthermore, the operator has a higher freedom of movement compared to the known treatment systems, on the other hand without having to move either the treatment apparatus 100 or the treatment device 1.

Therefore, other risks of damage for the patient are prevented.

Therefore, the invasiveness of the intervention is remarkably reduced.

Thus, the operator actuates the electrode 11, which had previously been connected to the radio frequency generator through the attachment element 21, so that the electrode 11 and the treatment tip 16 become electrically active and allow the reduction of the volume of the hypertrophic ligament through the specific currents and frequencies that vaporize the ligamentous tissue.

In the case that additional areas of ligamentum flavum are to be treated, it is possible to retract the device 1 within the treatment apparatus 100, to further move in the already described ways the catheter 300 until identifying a new area to be treated, then to extract again the treatment device 1 from the apparatus 100 and proceed in the already described ways to carry out the treatment of the ligamentum flavum.

Furthermore, as stated, it is possible to connect further epidural treatment devices to the apparatus 100 to carry out other types of treatment as required.

Although the use of the treatment device of the invention has been described in association with an endoscopic treatment apparatus, such device will also be used by itself.

In this case, the device will be advantageously provided with a catheter as the one of the treatment apparatus 300; consequently, the hand grip 2 will be provided with members for the actuation of the catheter 300.

Thus, the catheter 300 will be provided with two longitudinal channels, one for the viewing element and the other one for the cannula 10.

The catheter 300 will be inserted into the epidural channel in the previously described ways, and, once it reaches the area to be treated, the position of the catheter will be fixed and the actuation of the cannula and electrode in the previously described ways will be provided.

The invention claimed is:

1. A device for treating a ligamentum flavum, of a patient, by radio frequency, the device comprising:
a hand grip having a body configured to be held by an operator,
a cannula fixed at a proximal end thereof to said hand grip and extending longitudinally from said hand grip to an opposed distal end of the cannula, said cannula being arranged for reaching said ligamentum flavum;
at least one electrode which is electrically connectable to a radio frequency generator and is slidably housed in said cannula;
said cannula being provided with a hole to allow said electrode to emerge from said cannula;
an actuating device of said electrode being provided in said hand grip for moving said electrode, said actuating device comprises:
a slider slidable along a sliding guide, said slider actuable along said sliding guide to slide said electrode into along a longitudinal axis in said cannula;
a cavity defined on the body at the sliding guide configured to direct the sliding of the slider, said cavity having a first sliding portion and a second sliding portion coaxial therewith defining two sliding portions for the slider, said first portion being shaped so as to allow an axial translation of said slider along said guide to generate a consequent translation of said electrode in said cannula, and said second portion being configured so as to allow a radial translation of said slider, independent of said handgrip, along said guide so as to generate a corresponding radial translation of said electrode outside and independent of said cannula.

2. The device according to claim 1, wherein said second portion has such an extension as to allow a rotation of said slider through an angle in a range from about 90° to about 180°, or between 90°-270°.

3. The device according to claim 1, wherein said hole is provided on an outer wall of said cannula at a distance from a distal end thereof and is shaped to allow passage therethrough of said electrode.

4. The device according to claim 1, wherein said electrode has a diameter in the range from 0.4 mm to 1.3 mm, and is made of stainless steel.

5. The device according to claim 1, wherein said electrode is provided at an end portion thereof with a treatment tip configured to interact with a tissue to be treated, having a spherical shape.

6. The device according to claim 5, wherein said electrode comprises an electrified wire, positioned inside said electrode and made of a deformable material designed to impart a desired angulation to said end portion.

7. The device according to claim 6, wherein said electrified wire is made of: a nickel/titanium-based metal alloy, a super-elastic nickel/titanium metal alloy having shape memory, or stainless steel.

8. The device according to claim 1, further comprising a sheath slidably housed in said cannula and being internally hollow, so that it can slidably house said electrode, the sheath being made of insulating material, selected from the group consisting of: polyamide, polypropylene, PVC, and thermoplastic elastomer (TPE).

9. The device according to claim 8, further comprising an additional actuating device for moving said sheath in said cannula independently of said electrode.

10. The device according to claim 1, comprising a reinforcing sheath housed in said cannula coaxially thereto and arranged so as to reinforce a distal portion of said cannula.

11. The device according to claim 10, wherein said reinforcing sheath comprises a tubular body in which said electrode is slidably housed, and a reinforcing appendix which is curved or inclined with respect to a longitudinal axis of said cannula extending from the tubular body and configured to reinforce said electrode and to direct movement thereof.

12. An endoscopic treatment apparatus comprising a handle configured to be grasped by an operator; a catheter fixed at a first proximal end thereof to said handle and configured to be inserted into an endoscopic channel, said catheter being internally hollow and provided with a pair of longitudinal channels parallel to a longitudinal axis X' thereof; control members operatively connected to said catheter and configured to move said catheter; a plurality of connecting elements configured to connect said treatment apparatus to at least one endoscopic treatment device; and at least one connecting channel to connect each connecting element to at least one of said longitudinal channels to enable said treatment to be carried out, wherein said at least one endoscopic treatment device comprises:

a hand grip having a body configured to be held by an operator, a cannula fixed at a proximal end thereof to said hand grip and extending longitudinally from said hand grip to an opposed distal end of the cannula, said cannula being arranged for reaching said ligamentum flavum;

at least one electrode which is electrically connectable to a radio frequency generator and is slidably housed in said cannula;

said cannula being provided with a hole to allow said electrode to emerge from said cannula;

a actuating device of said electrode being provided in said hand grip for moving said electrode, said actuating device comprises a slider slidable along a sliding guide, for being actuated by an operator so as to be moved along said sliding guide to slide said electrode along a longitudinal axis in said cannula, a cavity defined on the body at the sliding guide configured to direct the sliding of the slider, said cavity having a first sliding portion and a second sliding portion coaxial therewith defining two sliding portions for the slider, said first portion being shaped so as to allow an axial translation of said slider along said guide to generate a consequent translation of said electrode in said cannula, and said second portion being configured so as to allow a radial translation of said slider, independent of said hand grip along said guide so as to generate a corresponding radial translation of said electrode outside and independent of said cannula.

13. The apparatus according to claim 12, further comprising a viewing element slidably housed in the other longitudinal channel.

14. The apparatus according to claim 13, wherein said viewing element is a flexible optical fiber.

* * * * *

UNITED STATES PATENT AND TRADEMARK OFFICE
CERTIFICATE OF CORRECTION

| | |
|---|---|
| PATENT NO. | : 10,945,785 B2 |
| APPLICATION NO. | : 15/455813 |
| DATED | : March 16, 2021 |
| INVENTOR(S) | : Giovanni De Polo |

It is certified that error appears in the above-identified patent and that said Letters Patent is hereby corrected as shown below:

In the Claims

In Claim 1, at Column 16, Line 35, after the letters "trode", and before the word "along", delete the word "into".

Signed and Sealed this
Twentieth Day of April, 2021

Drew Hirshfeld
*Performing the Functions and Duties of the
Under Secretary of Commerce for Intellectual Property and
Director of the United States Patent and Trademark Office*